United States Patent
Weisman et al.

(12) 
(10) Patent No.: US 6,479,063 B2
(45) Date of Patent: *Nov. 12, 2002

(54) THERAPEUTIC USES OF HORMONAL MANIPULATION USING COMBINATIONS OF VARIOUS AGENTS TO TREAT ATHEROSCLEROSIS

(76) Inventors: Kenneth Weisman, 30 Springton Pointe Dr., Newtown Square, PA (US) 19073; Michael E. Goldberg, 20 Aspen Dr., Ivyland, PA (US) 18974

( * ) Notice: Subject to any disclaimer, the term of this patent is extended or adjusted under 35 U.S.C. 154(b) by 0 days.

This patent is subject to a terminal disclaimer.

(21) Appl. No.: 09/747,653

(22) Filed: Dec. 26, 2000

(65) Prior Publication Data

US 2002/0006399 A1 Jan. 17, 2002

Related U.S. Application Data

(60) Provisional application No. 60/173,204, filed on Dec. 27, 1999.

(51) Int. Cl.[7] ........................... A61K 38/09; C07J 41/00; C07D 233/02
(52) U.S. Cl. ........................ 424/422; 424/423; 424/449; 424/464; 514/2; 514/15; 514/26; 514/385; 514/393; 514/646; 514/649; 514/656; 530/313; 530/328; 540/2; 540/120; 548/125; 548/300.1; 548/354.1; 552/9
(58) Field of Search ................. 424/464, 422, 424/423, 449; 514/2, 15, 26, 385, 393, 646, 649, 656; 530/313, 328; 540/2, 120; 552/9; 548/125, 300.1, 354.1

(56) References Cited

U.S. PATENT DOCUMENTS

| | | | | |
|---|---|---|---|---|
| 6,099,851 A | * | 8/2000 | Weisman et al. | 424/423 |
| 6,140,315 A | * | 10/2000 | Weisman et al. | 514/177 |
| 6,197,337 B1 | * | 3/2001 | Weisman et al. | 424/464 |

FOREIGN PATENT DOCUMENTS

CA  2232125  * 9/1998

* cited by examiner

Primary Examiner—Christopher S. F. Low
Assistant Examiner—Anish Gupta
(74) Attorney, Agent, or Firm—Caesar, Rivise, Bernstein, Cohen & Pokotilow, Ltd.

(57) ABSTRACT

A method of decreasing atherosclerosis and its complications involving administering to a human or animal various combinations of medications with Finasteride, Bicalutamide, Flutamide and Nilutamide.

12 Claims, No Drawings

THERAPEUTIC USES OF HORMONAL MANIPULATION USING COMBINATIONS OF VARIOUS AGENTS TO TREAT ATHEROSCLEROSIS

This application claims the benefit of the filing date of Dec. 27, 1999 of Provisional Patent Applications Ser. No. 60/173,204.

BACKGROUND OF THE INVENTION

Finasteride, a synthetic 4-azasteroid compound, 4-azaandrost-1-ene-17-carboxamide, N-(1,1-dimethylethyl)-3oxo-(5alpha 17beta)-. The empirical formula is C23H36N2O2. Finasteride is sold under the trade name Proscar, as identified by U.S. Pat. No. 5,175,155, the entire disclossure is incorporated by reference herein, is known for use in treatment of prostatic carcinoma.

Bicalutamide, a non-steroidal anti-androgen, chemical name is propanamide, N-[14-cyano-3-(trifluoromethyl) phenyl]-3-[(4-fluorophenyl)sulfonyl]-2-hydroxy-2-methyl-(+-), sold under the trade name Casodex, as identified by U.S. Pat. No. 4,636,505, the entire disclosure is incorporated by reference herein, is known for use in treatment of prostatic carcinoma.

Flutamide, an acetanilid, nonsteroidal antiandrogen having the chemical name, 2-methyl-N-[4-nitro-3-(trifluoromethyl)phenyl] propanamide, sold under the trade name Eulexin, as identified by U.S. Pat. Nos. 3,995,060, and 4,474,813, the entire disclosure of which are in corporarted by reference herein, Flutamide is known for use in treatment of prostatic carcinoma.

Nilutamide, a nonsteroidal, orally active, antiandrogen, having the chemical name 5,5-dimethyl 3-[4-nitro 3-(trifluoromethyl)phenyl] 2,4-imidazolidinedione, sold under the trade name Nilandron, as identified by U.S. Pat. No. 5,023,088, the entire disclosure is incorporated by reference herein, is known for usee in the treatment of prostatic carcinoma.

Goserelin Acetate, a synthetic decapeptide of LHRH or GnRH, chemical structure is pyro-Glu-His-Trp-Ser-Tyr-D-Ser(Bu)-Leu-Arg-Pro-Azgly-NH2 acetate [C59H84N18O14 (C2H4O2)x wherex=1 to 2.4] sold under the trade name Zoladex, as identified by U.S. Pat. No. 5,510,460, the entire disclosure is incorporated by reference herein, is known ifor the treatment of prostatic carcinoma.

Leuprolide acetate is a synthetic nonapeptide of naturally occurring gonadotropin-releasing hormone (GnRH or LHRH), the chemical name is 5-oxo-L-prolyl-L-histidyl-L-tryptophyl-L-seryl-L-tyrosyl-D-leucyl-L-leucyl-L-arginyl-N-ethyl-L-prolinamide acetate (salt) sold under the trade name Lupron or Lupron Depot, as identified by U.S. Pat. No. 4,897,256, the entire disclosure is incorporated by reference herein, is known for use in treatment of prostatic carcinoma.

Abarelix is a synthetic LHRH antagonist, the chemical name is N-Acetyl-3-(2-naphthyl)-D-alanyl-4-chloro-D-phenylalanyl-3-(3-pyridyl)-D-alanyl-L-seryl-N-methyl-L-tyrosyl-D-asparaginyl-L-leucyl-N6-isopropyl-L-lysyl-L-prolyl-D-alanylamide, manufacturer Praecis Pharmaceuticals Inc, the entire disclosure is incorporated herein, is known for use in treatment of prostatic carcinoma.

The present invention involves the use of combinations of these drugs in the prevention and treatment of 1) atherosclerosis
2) coronary artery disease
3) stroke
4) peripheral vascular disease Inhibition of testosterone metabolism is important in control of prostatic carcinoma and benign prostatic hypertrophy. We have observed a decrease in atherosclerosis and coronary artery heart disease in patients to whom inhibitors of testosterone metabolism have been administered. This effect has been demonstrated both in patients taking finasteride for benign prostatic hypertrophy and in patients taking several LHRH or GnRH inhibitors for prostatic carcinoma. We conclude that testosterone metabolism plays a role in the development of atherosclerosis and its complications including coronary artery disease, and that by blocking testosterone metabolism the disease was treated and/or prevented.

In the treatment of prostatic carcinoma it has been demonstrated that when using inhibitors of LHRH secretion (Leuprolide, Goserelin) that addition of various anti-androgens; Bicalutamide, Nilutamide, and Flutamide, result in a lower serum testosterone. In addition it has been shown that the use of Finasteride with oral anti-androgens (Bicalutamide, Nilutamide, Flutamide) can suppress testosterone metabolism and control prostatic carcinoma. Our invention involves the use of these combinations for a new use, treatment/prevention of atherosclerosis and its complications including coronary artery disease.

The data which leads us to conclude that suppression of testosterone metabolism can result in lower rates of atherosclerosis and its complications including coronary artery disease is presented below:

It was observed that patients to whom finasteride was being administered for treatment of benign prostatic hypertrophy seemed to have a lower incidence of atherosclerosis and heart disease.

Finasteride was being administered at a dosage of a single oral 5 mg tablet a day. This is the same tablet used in treatment of BPH as disclosed in U.S. Pat. No. 5,175,155 and such dosage applies in the present invention. However, use of a 2 mg or 10 mg oral tablet is contemplated.

Two studies were undertaken to determine whether finasteride was, in fact, effective in lessening the incidence of heart disease and other complications of atherosclerosis.

The result of the first study is as follows; A list of patients diagnosed with benign prostatic hypertrophy in late 1992 and 1993 was located. Treatment had been initiated with either finasteride or another oral agent of a different class (alpha-blocker). Patients were then contacted and an interval history was taken. In the control group of 45 subjects, 7 events (either cardiac bypass or heart attack) occurred in 6 subjects over 288 subject-years. In the finasteride treated group of 22 subjects there were no events over 61 subject-years. (Some patients had discontinued the use of finasteride, and only those on the drug for at least a year were considered.) We believe significantly more events occurred in the control group compared to the finasteride treated group. (95% Cl equal to 0.65% to 4.2%).

In the second study patients of the practice were given a questionnaire. Various patients had been treated with finasteride for varying lengths of time. Only those on the drug for at least one year were considered. The average time on finasteride was 3 years. The number of cardiac events occurring in the patients taking finasteride was only 4 events over 242 patient-years. (1.6%/yr.) In the control group 26 events occurred in the 3 years prior over 732 patient-years. (3.5%/yr.)

The 45% decrease observed in cardiac events is believed to be significant. (90% Cl equal to 1.4% to 3.7%).

Another retrospective study was performed which compared the rates of patient reported heart attack in several groups 1—control group of males entering the urology office for any routine complaint. 2—a group of prostate cancer patients treated with Leuprolide acetate, a LHRH inhibitor. 3—a group of prostate cancer patients treated with Goserelin acetate (Zoladex), a LHRH inhibitor. 4—a group of prostate cancer patients not treated with hormonal manipulation (neither Leuprolide or Goserelin). 5—all patients on LHRH inhibitors (group 2+group 3).

The patients on either Leuprolide or Goserelin were treated with the recommended doses indicated for the treatment of prostatic carcinoma, at either one or three month intervals depending on the preparation used. Leuprolide was dosed at 7.5 mg monthly (single intramuscular injection) or at 22.5 mg at 3 month intervals (single intramuscular injection). Goserelin was dosed at 3.6 mg monthly or at a dose of 10.8 mg at 3 month intervals (subcutaneous injection).

The various groups of office patients were evaluated by chart reveiw. In groups 2 and 3 only those on drug for at least one year were considered. Cardiac event is defined either the history of a heart attack or occurrence of coronary artery bypass or angioplasty. In control groups only events occurring in the 3 years prior to the questionnaire are charted. The results were as follows:

|  | Cardiac | | | |
| --- | --- | --- | --- | --- |
|  | No Patients | Events | Subject Years | Events/Year |
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 (Lupron) | 28 | 1 | 118 | .00847 |
| Group 3 (Zoladex) | 25 | 1 | 62 | .0161 |
| Group 6 (antiLHRH) groups 2 + 3 | 50 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (Lupron) and Total Control is 0.253. 95% Confidence Interval for the difference between the proportions is 0.00514 and 0.0454. Patients treated with Leuprolide acetate had fewer heart attacks than controls.

The observed difference between the proportions of Group 3 and Total Control is 0.0177. Patients treated with Goserelin (Zoladex) had fewer heart attacks than controls.

In the practice of the invention the medications may be administered as a tablet, or as a part of a liquid solution or dispersion, or patch or subcutaneous pellet in order to achieve systemic absorption of the drug.

It should be understood that this invention will apply to the administration of the medications in any form for the purpose of systemic absorption for the purpose of treating, and preventing atherosclerosis and its complications including but not limited to myocardial infarction, stroke, and peripheral vascular disease. Such forms will include not only tablets, but also subcutaneous pellets or cutaneous patches or other forms resulting in systemic availability of the drug. The active ingredient can be administered as a liquid in the form of a solution or a dispersion using appropriate solvents and preservatives as well as adjusting the pH to the range of maximum stability.

In the formulation of either solid or liquid pharmaceutically acceptable inactive ingredients may be used. These include excipients, preservatives or flavorings.

Methods of manufacturing finasteride are disclosed in U.S. Pat. Nos. 4,760,071 and 5,468,860.

Obviously these dosages can be varied depending upon experience in administering the drugs or as other conditions may dictate. The invention is not limited to any particular dosage or tablet size or frequency of dose or mode of administration. Also, forms may include tablets, suspensions, or pellets, which may be given orally or as intramuscular injections, or administered as subcutaneous pellets. Cutaneous patches may also be used. The active ingredient can be administered as a liquid, such as forming a solution or dispersion using an appropriate solvent or solvents.

Without further elaboration the foregoing will so fully illustrate our invention that others, may, by applying current future knowledge, adopt the same for use under various conditions of service

What is claimed is:

1. A method of decreasing atherosclerosis and its complications, said method comprising administering to a human or animal an amount sufficient to decrease atherosclerosis and its complications a combination of medications selected from the group consisting of:
 a) finasteride and bicalutamide;
 b) finasteride and flutamide;
 c) finasteride and nilutamide;
 d) finasteride and goserelin acetate;
 e) finasteride and leuprolide acetate;
 f) finasteride and Abarelix;
 g) bicalutamide and goserelin acetate;
 h) bicalutamide and leuprolide acetate;
 i) bicalutamide and Abarelix;
 j) flutamide and goserelin acetate;
 k) flutamide and leuprolide acetate;
 l) flutamide and Abarelix;
 m) nilutamide and goserelin acetate;
 n) nilutamide and leuprolide acetate; and
 o) nilutamide and Abarelix.

2. The method in claim 1 wherein the effective amount of Finasteride and dosing is a single 5 mg tablet taken orally once a day.

3. The method in claim 1 wherein the effective amount of Bicalutamide and dosing is a single 50 mg tablet taken orally once a day.

4. The method in claim 1 wherein the effective amount of Flutamide and dosing is two 125 mg tablets taken orally three times a day.

5. The method in claim 1 wherein the effective amount of Nilutamide and dosing is a 50 mg tablet taken orally three times a day.

6. The method in claim 1 wherein the effective amount of Goserelin and dosing is a single 3.6 mg subcutaneous implant taken once a month.

7. The method in claim 1 wherein the effective amount of Leuprolide acetate and dosing is a single 7.5 mg depo IM injection taken once a month.

8. The method in claim 1 wherein the effective amount of Abarelix and dosing is 30–50 ug/kg/day subcutaneously, or 3.0 mg/kg/month as a depot formulation administered intramuscularly.

9. The invention in claim 1 wherein the medications are administered as a tablet, or as a part of a liquid solution or dispersion, or patch, or subcutaneous pellet in order to achieve systemic absorption.

10. The method of claim 1 wherein the method of decreasing atherosclerosis and its complications involves myocardial infarction.

11. The method of claim 1 wherein the method of decreasing atherosclerosis and its complications involves stroke.

12. The method of claim 1 wherein the method of decreasing atherosclerosis and its complications involves peripheral vascular disease.

* * * * *